United States Patent [19]

Heineman et al.

[11] Patent Number: 4,894,253
[45] Date of Patent: Jan. 16, 1990

[54] METHOD FOR PRODUCTION OF COATED ELECTRODE

[75] Inventors: William R. Heineman; James E. Mark, both of Cincinnati, Ohio; Emory S. Decastro, Emeryville, Calif.; Christos Galiatsatos, Cincinnati, Ohio

[73] Assignee: University of Cincinnati, Cincinnati, Ohio

[21] Appl. No.: 229,720

[22] Filed: Aug. 8, 1988

Related U.S. Application Data

[62] Division of Ser. No. 895,782, Aug. 12, 1986.

[51] Int. Cl.$^4$ .............................................. B05D 3/06
[52] U.S. Cl. ....................................... 427/36; 427/44; 427/54.1; 427/58; 427/346; 427/421; 427/435
[58] Field of Search .................... 427/36, 35, 38, 44, 427/54.1, 58, 409, 388.2, 346, 421, 435

[56] References Cited

U.S. PATENT DOCUMENTS 4,184,001 1/1980 Hildreth ............................ 427/36 X Primary Examiner—Bernard Pianalto
Attorney, Agent, or Firm—Frost & Jacobs

[57] ABSTRACT

An electrode having a coating comprising at least two layers, at least one layer being a polymer network cross-linked by high energy radiation or chemically, and a method of producing such an electrode. The electrode is useful as a sensor for molecular oxygen, or as an ampermometric sensor with an enzyme or antibody immobilized in the cross-linked polymer layer.

19 Claims, 2 Drawing Sheets

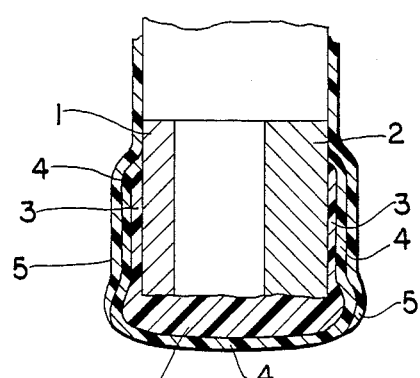
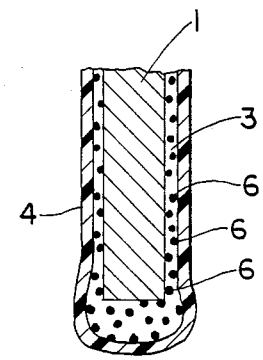
FIG. 1
FIG. 2
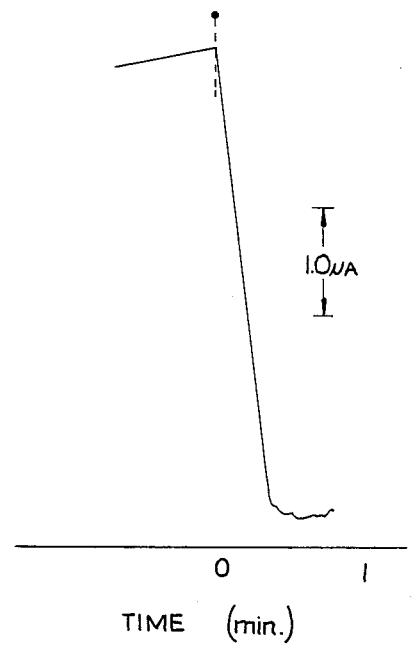
FIG. 4

METHOD FOR PRODUCTION OF COATED ELECTRODE

This is a division of application Ser. No. 895,782, filed Aug. 12, 1986.

BACKGROUND OF THE INVENTION

This invention relates to an electrode having a coating on an electroconductive core, the coating comprising at least two layers with at least one of the layers being a polymer network cross-linked by high energy radiation or a polymer network produced by end linking functionally terminated chains, or a polymer network produced by crosslinking chains having reactive functional groups as side chains. The electrode of the invention has particular utility as a sensor for molecular oxygen, or as an amperometric sensor having an enzyme or antibody immobilized in the cross-linked polymer layer.

The method of producing an electrode in accordance with the invention is simple and inexpensive in comparison to prior art practices. Moreover, the method is adapted to the fabrication of miniaturized electrodes, which is a feature generally recognized as being desirable but not hitherto attainable.

An oxygen sensor electrode of the invention exhibits enhanced response time as compared to presently available electrodes. An amperometric sensor electrode in accordance with the invention, when used as an electroanalytical device, exhibits enhanced response time, selectivity and sensitivity, i.e. low detection limits.

The Clark electrode, disclosed in U.S. Pat. Nos. 3,380,905; 3,539,455; and 3,912,386, is widely used for the determination of oxygen. It comprises a conducting metal such as platinum and a reference electrode mounted behind a thin membrane with a thin layer of electrolyte sandwiched between the membrane and the electrodes. Oxygen in a sample to be analyzed diffuses through the membrane and electrolyte layer to the metal electrode where it is detected by reduction. The membrane is critical in providing selectivity for oxygen by allowing only gases to pass therethrough, and it protects the electrode surface against fouling by preventing surfactants and other adsorbing species from reaching the electrode surface. The membrane may be polytetrafluoroethylene, silicone, methyl methacrylate, or cellulose acetate. Although highly successful, the Clark electrode has the disadvantages of relatively slow response time (due to the distance through the membrane and quiescent electrolyte layer which the oxygen must traverse to reach the electrode surface), and difficulty in miniaturization using conventional membrane-spacer construction.

L. C. Clark, Jr. et al, in "Rapid Micromeasurement of Lactate in Whole Blood", *Critical Care Medicine*, 12(5), 461–464 (1984) describe a lactate sensor comprising a very thin layer of lactate oxidase (immobilized by glutaraldehyde) held between a cellulose ester membrane and a polycarbonate membrane, cemented in an O-ring and held in place against an electrode tip.

Cross-linking of a polymer by radiation, such as ultraviolet radiation, gamma ray irradiation and the like, is well known and is disclosed, e.g., by E. S. Decastro et al in "Electrodes Coated With Polymer Networks Cross-Linked By γ-Irradiation" *J. Electroanal. Chem.* 138, 197–200 (1982).

In the Decastro et al article gamma irradiation of platinum electrodes coated with diallyl dimethyl ammonium chloride (DDAC) and 2,6-dichlorophenolindophenol (DCIP) is disclosed. Cross-linking of electroactive DCIP into an inert DDAC network was shown by cyclic voltammagrams.

Additionally, five articles disclosing entrapment of an enzyme by irradiation have been authored by H. Maeda et al, four being published in *Biotechnology And Bioengineering*, John Wiley and Sons, Inc., publisher:

Maeda I "Preparation Of Immobilized Enzymes Using Poly (Vinyl Alcohol)" Vol., XV 607–609 (1973); Maeda II "Preparation Of Immobilized Enzymes By Electron-Beam Irradiation", Vol. XV 827–829 (1973); Maeda III "Preparation Of Immobilized Enzymes By N-Vinylpyrrolidone And The General Properties Of The Glucoamylase Gel", Vol. XVI 1517–1528 (1974); Maeda IV "Preparation Of Immobilized β-Galactosidase By Poly (vinyl Pyrrolidone) And The Continuous Hydrolysis Of Lactose In Acid Whey", Vol. XVII 1571–1589 (1975). Maeda V is entitled "Preparation Of Immobilized Enyzmes By γ-Ray Irradiation", and published in *Biochimica et Biophysica Acta*, 315, 18–21 (1973).

In Maeda I immobilization of glucoamylase and invertase in polyvinyl alcohol is disclosed, using gamma ray irradiation of than 4M rad for cross-linking. However, 75–80% of the enzyme activity of glucoamylase and 80–90% of the enzyme activity of invertase were lost. There is no suggestion of utilizing this procedure for an electrode.

In Maeda II immobilization of glucoamylase and invertase in polyvinyl alcohol is disclosed, using electron beam irradiation in a nitrogen atmosphere. Over 50% of the enzyme activity was lost on entrapment by electron beam irradiation with 6 Mrad. As the radiation level was increased, enzyme activity decreased substantially. At 36 Mrad there was almost no enzyme activity.

In Maeda III immobilization of glucoamylase, invertase and β-galactosidase in vinyl pyrrolidone is disclosed, using gamma ray irradiation. Over 90% of enzyme activity was lost with invertase and β-galactosidase, while 55% activity was lost with glucoamylase.

In Maeda IV immobilization of β-galactosidase in polyvinyl pyrrolidone is disclosed using gamma ray irradiation. At radiation of 3.0 Mrad the activity of the enzyme was about 30%. Leakage of enzyme from the gel was detected where the PVP-enzyme solution contained more than 1% of enzyme protein.

In Maeda V the immobilization of enzymes by gamma ray irradiation is disclosed. Rigid gels were prepared from acrylamide monomer, eliminating the need for a cross-linking reagent. Irradiation of invertase and β-galactosidase with 1 Mrad of gamma ray irradiation resulted in loss of 65–75% of enzyme activity. Irradiation of glucoamylase with 2M rad of gamma ray irradiation resulted in a 60% loss of enzyme activity.

U.S. Pat. No. 3,940,667 issued Feb. 24, 1976 to G. R. Pearce, discloses an electrode with a polymer containing coating made by applying radiation curable polymer containing material to a metal containing electrode, irradiating the applied polymer containing material by ultraviolet or electron beam radiation, and introducing an electrolyte into the cured polymer.

U.S. Pat. No. 4,579,642, issued Apr. 1, 1986 to Y. Niiyama et al, discloses an electrochemical sensor comprising a vessel with a liquid-junction at an end face, a resilient ion selective membrane at the liquid-junction, and an immobilized enzyme membrane covering the ion selective membrane.

U.S. Pat. Nos. 4,404,066 issued Sept. 13, 1983 and 4,356,074 issued Oct. 26, 1982 to J. M. Johnson and European patent application No. 104,935 published Apr. 4, 1984 disclose an electrochemical cell laminate having exterior membrane layers and an interior enzyme layer. An electrode located within the enzyme layer applies an electrical potential to the enzyme.

U.S. Pat. No. 4,444,878 issued Apr. 24, 1984 to H. P. Paulus discloses an electrode, and a membrane thereon having associated therewith a plurality of molecules of each enzyme which acts on the substance to be measured and a plurality of bispecific antibody determinants bonded to the molecules of each enzyme.

Despite the considerable amount of work devoted to development of electroanalytical devices which include electrodes having an electrolyte or enzyme layer, there still exists a genuine need for an electrode, and a simple and inexpensive method for making it, which exhibits improved response time and selectivity, and low detection limits, and which can be readily miniaturized.

SUMMARY OF THE INVENTION

It is an object of the present invention to provide an electrode meeting the need mentioned above.

It is a further object to provide a method of making an electrode of any desired dimension in a simple and readily reproducible manner.

The above and other objects of the invention are achieved in an electrode comprising an electroconductive core and a coating thereon comprised of at least two layers, at least one of the layers being a polymer cross-linked by high energy radiation such as gamma rays, electron beams, neutrons or ultra-violet light, or by chemically crosslinking the chains through functional groups located at their ends or along their backbones.

In an embodiment of the invention adapted for use as a sensor for molecular oxygen, an inner layer is a cross-linked polyelectrolyte, and the outer layer is oxygen permeable and solution impermeable. Preferably the outer layer is also a cross-linked polymer.

In another embodiment adapted for use as an amperometric sensor, an inner layer is a cross-linked polymer having an immobilized enzyme or an immobilized antibody uniformly dispersed and permanently bonded within the polymer. An outer layer is a liquid permeable material which is preferably a polymer cross-linked by high energy radiation and which may function as or include a selective chemical film capable of retarding fouling of the electrode.

In accordance with the invention there is provided a method of producing an electrode which comprises applying to an electroconductive core a liquid inner layer and a liquid outer layer which are immiscible with one another, at least one of the layers being polymerizable, and cross-linking the polymerizable layer by high energy radiation. The radiation dose controls the "pore size" of the resulting polymer network The polymerizable layer can also be cross-linked by the chemical method whereby functionally terminated chains are end linked. In this case the length of the terminated chains controls the "pore size" of the network. Another chemical method would involve crosslinking (with optional use of a peroxide catalyst) through functional groups appearing as side chains on the polymer. In this case, the spacing of the groups along the chain would control the pore size. Another chemical technique involves crosslinking chains even without reactive functional groups through generation of free radicals, e.g. by heating a peroxide or other unstable organic compound.

Preferably the outer layer is also polymerizable by irradiation, and both layers may be cross-linked simultaneously after application by radiation. Alternatively, the inner layer may be cross-linked first, followed by application of the outer layer.

BRIEF DESCRIPTION OF THE DRAWINGS

FIG. 1 is a diagrammatic sectional view of an oxygen sensor electrode embodying the invention.

FIG. 2 is a diagrammatic, fragmentary sectional view of an amperometric enzyme or antibody electrode embodying the invention.

FIG. 4 is a typical amperometric response of an electrode of the invention irradiated at 5 Mrad.

DETAILED DESCRIPTION OF THE INVENTION

Figure 3:
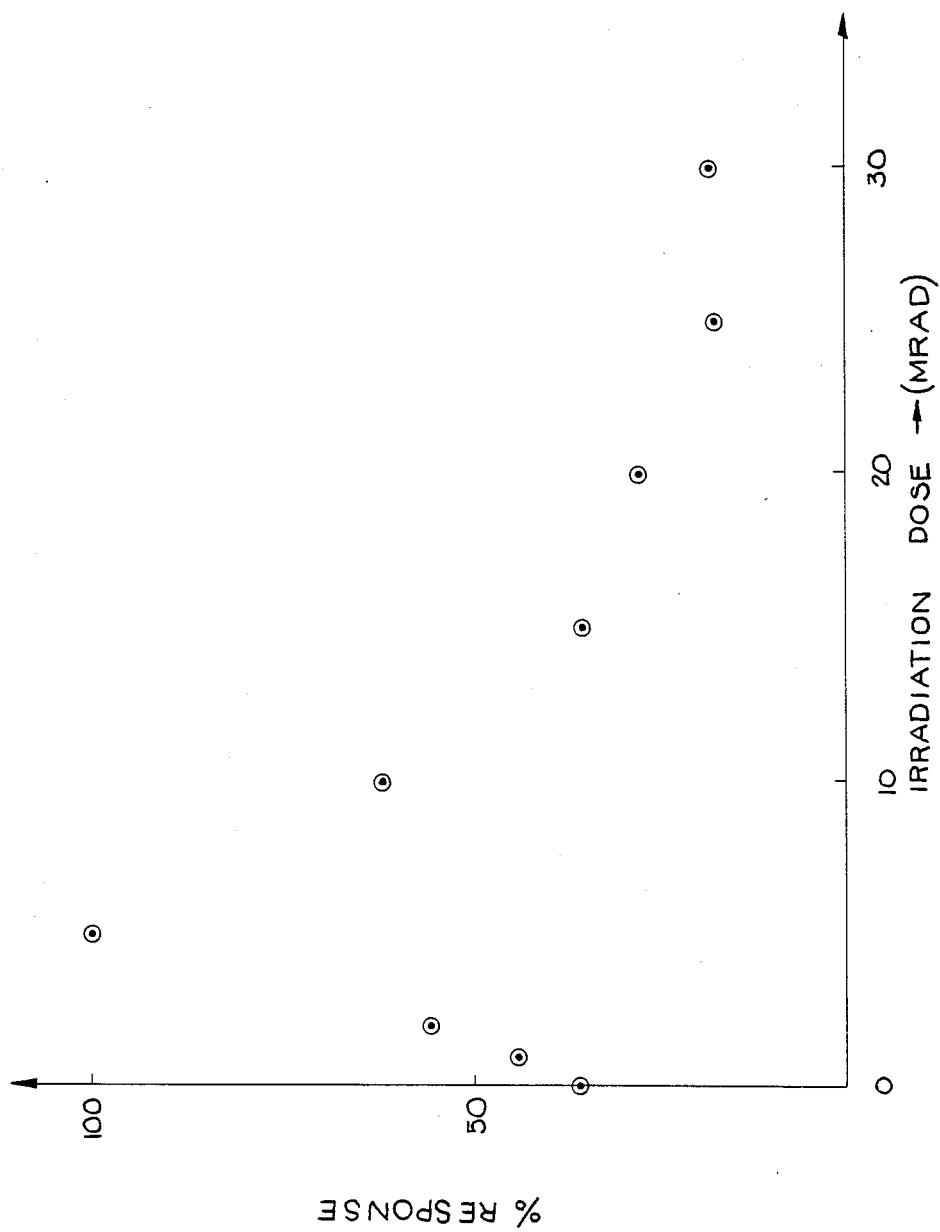
FIG. 3 is a graphic representation of the electrochemical response of an enzyme electrode of the invention at various radiation doses.

An electroconductive core for the electrode of the invention may be a metal such as platinum or gold, or graphite or glassy carbon.

At least one of the layers of the coating on the core is a cross-linked polymer. In the embodiment adapted for use as an oxygen sensor, the inner layer is a cross-linked network of polyelectrolytes, which is hydrophilic, is capable of functioning as a supporting electrolyte in an electrochemical cell, and is formed from a monomer or polymer which can be cross-linked by high energy radiation. Although a number of polymers fall within this definition, an exemplary polymer is a quaternary ammonium ion polymer such as poly (vinylbenzyl trimethyl ammonium chloride). In this embodiment a hydrophobic outer layer is preferably also a cross-linked polymer which is permeable to oxygen but excludes other species present in solution such as hydrated ionic species in the sample solution being analyzed. This outer layer is composed of a material capable of polymerizing by high energy radiation or other cross-linking techniques, for example, chemical reagent (or ultra-violet cross-linking). Numerous polymers are satisfactory for this purpose, and a polymerized dimethyl siloxane has produced excellent results. It is within the scope of the invention to incorporate a redox couple in the polyelectrolyte inner layer.

The polymer films on the electroconductive core are formed by simply dipping the core into a solution and then cross-linking, as explained in detail hereinafter. Methods other than dipping can be used just as easily, for example, spraying, spin coating and the like. These methods produce very thin polymer layers, which in turn results in a substantially improved response time because the distance which oxygen molecules must traverse in order to reach the electrode surface is minimized.

In an embodiment adapted for use as an amperometric sensor, an inner layer of the coating on the electroconductive core is a cross-linked polymer having an enzyme or an antibody dispersed therein and permanently entrapped or bonded within the polymer layer. A biocompatible polymer formed by high energy radiation does not adversely affect the enzyme or antibody immobilized therein. Polyvinyl alcohol is an exemplary material. An outer layer is also provided which is a liquid permeable material. Preferably the outer layer is a polymer which may also have been cross-linked by high energy radiation. It may function as a selective chemical film capable of retarding fouling of the electrode.

Numerous enzymes such as glucose oxidase, galactose oxidase, alkaline phosphatase and the like can be immobilized in a polyvinyl alcohol layer. Antibodies such as the antibody for digoxin and the like can also be immobilized in a polyvinyl alcohol layer.

As will be shown hereinafter, a material which will cross-link at a low radiation dose is preferred in order to minimize denaturation of the enzyme or antibody. A polymer network which does not affect the desirable properties of the enzyme and/or antibody immobilized therein in such way as to render the electrode "non-functional" is also preferred. Polyvinyl alcohol meets these requirements and is therefore an ideal polymer for use on the inner layer.

In both the above-described embodiments, the inner layer and outer layer are different materials.

Irradiation can be effected by various means such as ultraviolet light, gamma rays, electron beams, neutrons and the like.

Referring to FIG. 1, a sensor is shown diagrammatically, comprising as the working electrode a platinum wire 1 and a silver/silver chloride reference electrode 2. Both electrodes are provided with an inner coating 3 of a cross-linked polymer which may be, for example, poly (vinylbenzyl trimethyl ammonium chloride). An outer layer 4 may be a polymerized dimethyl siloxane. Both layers 3 and 4 may essentially encapsulate the electroconductive core 1. For protection of the assembly a polymerized epoxy outermost layer 5 may be provided. A portion of layers 3 and 4 adjacent the tips of the wires is left uncovered by epoxy resin, and this exposed area serves as the sensing portion of the electrode.

Reference electrode 2 may be encapsulated in the same coating as the platinum wire 1 with the same inner and outer layers 3 and 4 and epoxy protective layer 5.

It will of course be understood that the reference electrode 2 need not be coupled to the working electrode 1 and can be fabricated separately therefrom. However, the embodiment illustrated in FIG. 1 provides a convenient and simple manner of coating both electroconductive cores simultaneously and forming a wire bundle.

Referring to FIG. 2, a portion of a single working electrode is illustrated diagrammatically, adapted for use as an amperometric sensor. As in FIG. 1, an electroconductive core 1 is provided, which may be platinum, gold or graphite. An inner layer 3 of polyvinyl alcohol cross-linked by radiation contains enzyme 6 immobilized, i.e. bonded or entrapped, within the polymer network. An outer layer 4 may be a network of cross-linked polymer with size exclusion or ionic properties to control access to the enzyme layer and thereby enhance selectivity.

Preparation of electrodes in accordance with the invention are described in the following examples, which are intended to be non-limiting:

EXAMPLE 1

An Ag/AgCl reference electrode was prepared by depositing a coating of silver chloride on a 2.5 cm length of 0.6 mm diameter silver wire. A potential of 9 volts was applied between the silver wire and a platinum wire dipped in saturated aqueous sodium chloride to form the silver chloride coating. A 2.5 cm length of 0.3 mm diameter platinum wire was taped to the Ag/AgCl reference wire with 1 mm clearance between the two wires, leaving about half the length of the wires uncovered by the tape.

An aqueous solution of vinylbenzyl trimethyl ammonium chloride (VTAC) was partially evaporated to obtain a syrupy consistency. The exposed electrode wires (i.e. the platinum working electrode and the Ag/AgCl reference electrode) were dipped in the thickened solution and spun to form an even coating. The coating was allowed to flow slightly to accumulate in the form of a small bead at the end of the wire bundle. The coating was then allowed to air dry.

A solution of poly (dimethyl siloxane) (PDMS) was prepared by adding 0.5 ml of PDMS to 1.0 ml of a vinyl endlinker (Dp=25) in toluene, adding 0.15 g of silica gel (200 mesh), equivalent to 10% by weight silica, and heating it. A 0.1% catalyst solution was prepared by mixing 50 μl of platinic acid with 7.5 ml toluene. The electrode assembly coated with VTAC was next dipped in the PDMS mixture allowing the coating to creep up past the VTAC coating. Immediately after dipping, two μl aliquots of the catalyst solution were applied, and the electrodes were spun to cause mixing between the PDMS and catalyst and to evaporate some of the toluene. The assembly was then oven dried for 10 minutes at 80° C. This sequence was repeated 4 times to give a total of 5 dip coats of PDMS. After the last coating the probe assembly was left in the oven for 30 minutes and then set overnight in air at room temperature.

Water was added to the encapsulated VTAC layer in order to make it conductive. This was done by poking a hole in the PDMS coating with a fine needle. The electrodes were connected to a DVM and then dipped in water. Penetration of water into the encapsulated VTAC layer was confirmed by measuring the resistance which decreased from infinite to about 100K ohm.

After the addition of water, an epoxy resin coating was applied to coat substantially the entire unit except for a portion of the bead (about a 2 square mm area) at the end of the wire bundles, this exposed bead area serving as the sensing portion of the electrode. The epoxy coating was a relatively heavy coating for the purpose of protecting the assembly and ensuring that the wires would not pull apart. The assembly was then dried over-night in air, and the resistance of the completed probe after drying was between 100 and 500K ohm.

Evaluation of the oxygen sensor prepared in the above manner was conducted by cycling the sensor initially in an Erlenmeyer flask which was filled either with ambient air or purged with argon. Chronoamperograms were obtained by alternatively stepping the potential from −0.4V to −1.4V vs Ag/AgCl in air, then in the argon filled flask. The potentials were held for 10 seconds each and a run consisted of 6 steps.

A calibration curve was constructed by using a series of oxygen-nitrogen mixtures (10, 51, 107 and 498 ppm) in the same Erlenmeyer flask with the gases being bubbled through water in the flask. The potential was stepped from open circuit to −0.5V vs Ag/AgCl with a Bioanalytical Systems amperometric LC−3 controller, and the resulting current was recorded on a strip chart recorder. Ambient air was also analyzed in addition to the gas mixtures. The area under the chronoamperogram peak in the first 24 seconds was used as the analytical signal. New mixtures were introduced for 3 to 6 minutes before stepping the potential, which was held for 5 minutes and then stepped back to open circuit for another 5 minutes before a new step was applied. This sequence was repeated four times, with the first run being used only for preconditioning the electrode.

The electrode was then used to monitor oxygen dissolved in blood plasma. Chronoamperometry was used to evaluate the electrode response. The electrode potential was stepped from open circuit to −0.6V vs SCE repetitively for 24 hours. This potential causes reduction of dissolved oxygen. The chronoamperograms for the electrode of the invention showed no fouling in the 24 hour period, but rather a slight increase in current response was observed. This increase in current response may have been due to increasing permeability of the film to oxygen.

By way of comparison, cyclic voltammograms of unmodified and uncoated platinum wires in blood plasma showed immediately fouling and poisoning of the platinum surface by adsorbed proteins.

Accordingly, oxygen permeability and solution impermeability were achieved.

The electrode of the invention was also found by further tests to exhibit no detectable permeability to potassium ferricyanide solution. Furthermore, the cross-linked PDMS films remained stable for polymer chain links of Dp equal to 25. However, it was found that longer chain links formed by vinyl end linkers with Dp greater than 25 did not remain stable on the platinum wire electrode.

The calibration curve obtained from the series of oxygen-nitrogen mixtures exhibited a linear plot from ambient air oxygen concentrations down to about 51 ppm. This limit compares favorably with other electrodes designed for the trace analysis of oxygen, for which 35 nm is a typical detection limit. Measurement deviation ranges from 2% to 10% RSD.

EXAMPLE 2

Graphite electrodes were polished with 600 grit silicon carbide paper, boiled in distilled water for 2 hours and dried at 80°–110° C. overnight.

Polyvinyl alcohol (100% hydrolyzed) having an average molecular weight of 8600 was dissolved in hot water, by adding 3.0 g of polyvinyl alcohol (PVAL) in 80 ml of water at 90° C., elevating the temperature to 100° C. and adjusting the volume to 100 ml. After stirring for about 10 minutes, 20 $\mu$l were applied on the surface of each electrode, and the electrode was spun at about 2000 rpm. 10 $\mu$l of 1 mg glucose oxidase in 3 ml water and 10 $\mu$l of PVAL solution were applied at intervals 15 minutes. The electrodes were then subjected to $\gamma$ irradiation from a 60° C. source varying from 0 to 30M rads, with an average flux of $7.4 \times 10^3$ to $8 \times 10^5$ rads/hour.

Electrochemical response was tested by dipping an electrode in saturated solutions of $\beta$-D-glucose and observing the hydrogen peroxide generated by holding the potential at +1200 mV, where hydrogen peroxide is oxidized. Each electrode was held for at least 2 hours in a stirred buffer solution in order to obtain the maximum extent of swelling.

FIG. 3 illustrates the electrochemical response of electrodes in accordance with the irradiation dose. Each point on the graph of FIG. 3 represents the average of 2 electrodes prepared under the same condition, or, if the difference was more than 10%, the average with a third electrode.

As the irradiation dose increases, the extent of cross-linking of PVAL increases, and this increases the probability for bonding and/or trapping of glucose oxidase into the PVAL network. On the other hand, the enzyme loses activity as the irradiation dose increases. These two antagonistic effects produced a maximum response at the 5 Mrad dosage level. However, even at 25 Mrads the immobilized enzyme showed a characteristic response. This indicates that the immobilized enzyme is more stable than the native enzyme which exhibits greater degradation at equivalent doses.

FIG. 4 represents a typical amperometric response of an electrode prepared in the manner described above which was subjected to $\gamma$ irradiation of 5M rad. It will be noted that the response time or rate is quite rapid.

For glucose oxidase-containing electrodes the maximum response occurred at about pH 6, which is about 0.5 pH unit more basic than the native enzyme.

The detection limit for electrodes subjected to $\gamma$ irradiation of 5M rad was 0.05 mM $\beta$-D-glucose.

Cyclic voltammetry did not show any evidence of direct glucose oxidation on the electrode.

Stability of the electrodes was found to be excellent. After testing for more than 60 days, no decay of response was observed.

EXAMPLE 3

Graphite electrodes prepared in the same manner as in Example 2 are dipped in a solution containing the antibody for digoxin mixed with PVAL, the solution being prepared in the same manner as in Example 2. The electrode is then exposed to two doses of $\gamma$ radiation of 2 Mrad. Retention of active antibody is tested by dipping the electrode in a solution of digoxin-alkaline phosphatase conjugate and allowing the conjugate to bind with immobilized antibody. The electrode is then immersed in a solution of phenylphosphate, and enzymatically generated phenol is detected by oxidation of phenol at +750 mV vs Ag/AgCl. Detection of a signal for phenol is indirect evidence that antibody is available for binding with antigen. This sequence of reactions is the basis of an electrochemical enzyme immunoassay for digoxin.

It is evident that electrodes in accordance with the invention exhibit rapid response time, good selectivity and high sensitivity. Moreover, the method of preparation described in Example 1 above could readily be adapted to the production of miniature electrode assemblies.

We claim:

1. A method of producing an electrode which comprises applying to an electroconductive core a liquid inner layer and a liquid outer layer by dipping, spraying or spin coating at a temperature not higher than about 100° C., said inner and outer layers being different materials, at least said outer layer being polymerizable, cross-linking said outer polymerizable layer in situ into a network, and controlling the pore size of said layer to obtain a permeable polymer network.

2. The method claimed in claim 1, wherein cross-linking is effected by high energy radiation.

3. The method claimed in claim 1, wherein cross-linking is effected chemically by means of end linkers to obtain functionally terminated chains having a length not exceeding a Dp of 25.

4. The method claimed in claim 1, wherein cross-linking is effected chemically by means of reactive functional groups located as side chains.

5. The method claimed in claim 1, wherein cross-linking is effected chemically by generation of free radicals from unstable organic compounds by thermal decomposition.

6. The method claimed in claim 5, wherein said unstable organic compounds are peroxides.

7. The method claimed in claim 1, wherein said inner layer is polymerizable, wherein said inner layer is cross-linked by high energy radiation, and thereafter said outer layer is applied.

8. The method claimed in claim 5, wherein said outer layer is cross-linked after application by high energy radiation.

9. The method claimed in claim 8, wherein cross-linking is effected by gamma ray irradiation.

10. The method claimed in claim 7, wherein said outer layer is poly (dimethyl siloxane).

11. The method claimed in claim 7, wherein said inner layer is poly (vinylbenzyl trimethyl ammonium chloride).

12. The method claimed in claim 11, wherein a redox couple is dispersed in said inner layer.

13. The method claimed in claim 7, wherein said inner layer is poly (vinyl alcohol) having one of an enzyme and an antibody dispersed therein.

14. The method of claim 13, wherein said radiation is of a dose capable of completely cross-linking the polymer and entrapping the enzyme in the polymer network, but not capable of destroying the activity of the enzyme.

15. The method claimed in claim 13, wherein said enzyme is glucose oxidase.

16. The method claimed in claim 13, wherein said outer layer functions as a selective chemical film capable of retarding fouling of said electrode.

17. The method claimed in claim 1, wherein said outer layer is a gas permeable, liquid impermeable material.

18. The method claimed in claim 1, wherein said inner layer is poly (vinylbenzyl trimethyl ammonium chloride).

19. The method claimed in claim 1, wherein said outer layer is a poly (dimethyl siloxane).

* * * * *